US005437192A

United States Patent [19]
Kawamoto et al.

[11] Patent Number: 5,437,192
[45] Date of Patent: Aug. 1, 1995

[54] PHYSICAL PROPERTY MEASURING DEVICE

[75] Inventors: Takeshi Kawamoto; Toshio Hrowatari; Eiji Tahara, all of Kitakyushu; Hiromasa Katayama, Joetsu, all of Japan

[73] Assignee: Mitsubishi Chemical Corporation, Tokyo, Japan

[21] Appl. No.: 138,070

[22] Filed: Oct. 20, 1993

[30] Foreign Application Priority Data

Oct. 20, 1992 [JP] Japan .................................. 4-281970
Oct. 20, 1992 [JP] Japan .................................. 4-281971

[51] Int. Cl.⁶ .................................................. G01N 33/00
[52] U.S. Cl. .................................... 73/826; 73/159; 73/160; 73/828; 73/831
[58] Field of Search ............... 73/826, 828, 831, 833, 73/834, 835, 837, 845, 846, 847, 848, 853, 160

[56] References Cited

U.S. PATENT DOCUMENTS

| | | | |
|---|---|---|---|
| 3,537,301 | 7/1968 | Hasenwinkle | 73/834 |
| 3,707,119 | 12/1972 | Cowan | 73/833 |
| 4,606,230 | 8/1986 | Scott et al. | 73/856 |
| 4,909,084 | 3/1990 | Knoff | 73/856 |
| 5,167,150 | 12/1992 | Shofner et al. | 73/160 |

*Primary Examiner*—Richard E. Chilcot, Jr.
*Assistant Examiner*—Max H. Noori
*Attorney, Agent, or Firm*—Oblon, Spivak, McClelland, Maier, & Neustadt

[57] ABSTRACT

A physical property measuring device for measurement of physical properties of a test sample piece in the form of a flexible sheet-like material is provided. The test sample piece is fed to a measuring zone of the device while being interposedly held at a whole upper end thereof between transfer arms so as to be kept hanging, to thereby minimize or substantially prevent application of any unnecessary external force thereto during transferring. In the measuring zone, the test sample piece is kept interposedly held at upper and lower portions thereof between upper clamp arms of an upper clamp mechanism and between lower clamp arms of a lower clamp mechanism and the upper and lower clamp mechanisms are actuated relative to each other to carry out measurement of desired physical properties.

9 Claims, 5 Drawing Sheets

PHYSICAL PROPERTY MEASURING DEVICE

BACKGROUND OF THE INVENTION

1. Field of the Invention

This invention relates to a physical property measuring device, and more particularly to a device for measuring physical properties of a flexible sheet-like test sample made of, for example, a flexible film or the like such as, tensile strength of the test sample or the like.

2. Discussion of the Background

In general, measurement of physical properties of a sheet-like test sample such as tensile strength thereof or the like by means of a physical property measuring device has been conventionally carried out in a manner to clamp the entire upper and lower ends of the test sample through a pair of upper clamp arms and a pair of lower clamps arranged in a measuring zone of the device, respectively, and then apply, to the clamp arms. A tensile force sufficient to cause the test sample to be ruptured, resulting in elongation of the test sample, a rupture point thereof or the like being continuously measured.

Also, measurement of physical properties of the sheet-like test sample such as the thickness thereof, tensile strength thereof or the like requires one to successively feed the test samples to the measuring zone of the physical property measuring device. For the purpose of feeding the test samples to the measuring zone for the measurement, a predetermined number of test samples are kept piled up on a sample stocker. Then, the test samples are laterally successively pushed out one by one from the bottom of the pile by means of an ejector pin. Alternatively, feeding of the test samples is carried out in such a manner that a predetermined number of test samples which are horizontally juxtaposed to one another are extracted one by one by suction through a suction pad in order from one side and then transferred to the measuring zone.

The conventional physical property measuring device exhibits a satisfactory function when the test sample has increased thickness and rigidity. However, when the test sample is made of a flexible sheet-like material such as a flexible film or the like, feeding of the test sample to the measuring zone and suction of the test sample by the suction pad cause the test sample to be deformed and/or wrinkled. Also, a test sample which is curved and/or statically electrified leads to a failure in suspension or hanging of the test sample. Thus, the conventional physical property measuring device fails to constantly carry out stable feeding of the test sample to the measuring zone and satisfactory clamping of the test sample by the clamp arms, leading to a failure in proper measurement of physical properties of the test sample.

Further, in the case that the test sample which is made of a flexible sheet material is clamped at the upper and lower ends thereof through each pair of upper clamp arms and lower clamp arms, fragments of the test sample ruptured in the test are caused to be adhesively held on one of the clamp arms in each pair when the clamp arms in each pair are actuated so as to be open with respect to each other. Thus, the prior art causes automatic removal of the fragments from the clamp arms to be highly difficult or substantially impossible. This is particularly noticeable when the test sample is made of a flexible film material of 1 to 50 μm in thickness, because the test sample is irregularly ruptured to a degree sufficient to fail to permit the fragments of the ruptured test sample to be satisfactorily removed from the clamp arms.

SUMMARY OF THE INVENTION

The present invention has been made in view of the foregoing disadvantages of the prior art.

Accordingly, it is an object of the present invention to provide a physical property measuring device which is capable of facilitating feeding of a test sample piece to a measuring zone of the device irrespective of the form of the test sample piece.

It is another object of the present invention to provide a physical property measuring device which is capable of effectively feeding a test sample piece in the form of a flexible sheet free of rigidity to a measuring zone of the device without causing deformation of the test sample piece or the like.

It is a further object of the present invention to provide a physical property measuring device which is capable of facilitating, after a test for physical properties of a test sample piece is completed, removal of fragments of the test sample piece ruptured in the test from clamp arms.

Generally speaking, the physical property measuring device of the present invention is directed to measurement of physical properties of a test sample piece in the form of a flexible sheet-like material such as a flexible film, wherein the test sample piece is fed to a measuring zone of the physical property measuring device while being kept hung so as to prevent application of any unnecessary external force thereto. The test sample piece is interposedly held at upper and lower clamped portions thereof between a pair of upper clamp arms and between a pair of lower clamp arms in such a manner that upper and lower ends of the test sample piece defined outward of the above-described upper and lower clamped portions of the test sample piece are free from clamping by the upper and lower clamp arms so as to facilitate removal of the test sample piece from the clamp arms after measurement of the physical properties.

It was found that when the test sample piece is fed from a sample stocker to the measuring zone while preventing any unnecessary external force from being applied to the test sample piece during extraction of the test sample piece from the sample stocker, feeding of the test sample piece to the measuring zone may be readily and stably accomplished, to thereby ensure measurement of the physical properties with high reliability.

Also, it was found that arrangement of a guide mechanism for guiding the test sample piece to the lower clamp arms permits the lower clamp arms to readily interposedly hold the lower clamped portion of the test sample piece therebetween even when the test sample piece to be tested is decreased in weight.

Further, it was found that employment of a removal mechanism which is adapted to be moved between an upper clamp mechanism and a lower clamp mechanism to remove fragments of the test sample piece ruptured in the test from the mechanisms by suction after completion of the measurement further promotes elimination of the above-described disadvantage of the prior art.

Accordingly, in accordance with the present invention, a physical property measuring device for measuring physical properties of a test sample piece of a flexible sheet-like material such as a flexible film or the like is provided. The physical property measuring device includes a measuring zone in which measurement of physical properties of the test sample piece is carried out, a transfer mechanism including a pair of transfer arms for transferring the test sample piece to the measuring zone to feed the measuring zone with the test sample piece while interposedly holding the test sample piece between the transfer arms to keep it hanging, and an upper clamp mechanism and a lower clamp mechanism arranged vertically opposite to each other in the measuring zone. The upper clamp mechanism includes a pair of upper clamp arms for interposedly holding an upper clamped portion of the test sample piece defined inward of an upper end of the test sample piece therebetween and the lower clamp mechanism includes a pair of lower clamp arms for interposedly holding a lower clamped portion of the test sample piece defined inward of a lower end of the test sample piece therebetween.

Also, in accordance with the present invention, a physical property measuring device for measuring physical properties such as tensile strength or the like of a test sample piece of a flexible sheet-like material such as a flexible film or the like is provided. The physical property measuring device includes a measuring zone in which measurement of physical properties of the test sample piece is carried out, a transfer mechanism including a pair of transfer arms and transferring the test sample piece to the measuring zone to feed the measuring zone with the test sample piece while interposedly holding the test sample piece between the transfer arms to keep it hanging, and an upper clamp mechanism and lower clamp mechanism arranged vertically opposite to each other in the measuring zone, wherein the upper clamp mechanism includes a pair of upper clamp arms for interposedly holding an upper clamped portion of the test sample piece positioned inward of an upper end of the test sample piece therebetween and the lower clamp mechanism includes a pair of lower clamp arms for interposedly holding a lower clamped portion of the test sample piece positioned inward of a lower end of the test sample piece therebetween subsequent to the holding of the upper clamped portion of the test sample piece by the upper clamp arms. The device also includes a guide mechanism for guiding the lower clamped portion of the test sample piece to the lower clamp arms subsequent to the above-described holding of the upper clamped portion of the test sample piece by the upper clamp arms and prior to the above-described holding of the lower clamped portion of the test sample piece by the lower clamp arms.

Further, in accordance with the present invention, a physical property measuring device for measuring physical properties such as tensile strength or the like of a flexible sheet-like test sample piece of a flexible sheet-like material such as a flexible film or the like is provided. The physical property measuring device includes a measuring zone in which measurement of physical properties of the test sample piece is carried out, a transfer mechanism including a pair of transfer arms and transferring the test sample piece to the measuring zone to feed the measuring zone with the test sample piece while interposedly holding the test sample piece between the transfer arms to keep it hanging, and an upper clamp mechanism and a lower clamp mechanism arranged vertically opposite to each other in the measuring zone, wherein the upper clamp mechanism includes a pair of upper clamp arms for interposedly holding an upper clamped portion of the test sample piece positioned inward of an upper end of the test sample piece therebetween and the lower clamp mechanism includes a pair of lower clamp arms for interposedly holding a lower clamped portion of the test sample piece positioned inward of a lower end of the test sample piece therebetween. The device further includes a removal mechanism for removing, from the clamp arms, fragments of the test sample piece ruptured due to measurement of the physical properties and kept held on the clamp arms.

Moreover, in accordance with the present invention, a physical property measuring device for measuring physical properties such as tensile strength or the like of a test sample piece of a flexible sheet-like material such as a flexible film or the like is provided. The physical property measuring device includes a measuring zone in which measurement of physical properties of the test sample piece is carried out and at least one sample stocker formed with a plurality of storage grooves for storing the test sample pieces therein and a plurality of cutouts, wherein the storage grooves are arranged in juxtaposition with each other and the cutouts are arranged so as to permit an extraction side of each of the storage grooves on which the test sample piece is extracted from the storage groove to be open through each of the storage grooves. The device also includes a sample extraction mechanism including holding arms and arranged so as to be accessible to each of the cutouts of the storage grooves, wherein the holding arms interposedly hold the test sample piece therebetween to outwardly extract it from the storage groove through the cutout. The device further includes a transfer and support mechanism arranged in proximity with the extraction side of the sample stocker for transferring the test sample piece extracted from the sample stocker while supporting it thereon, a transfer mechanism for transferring the test sample piece to the measuring zone while keeping the test sample piece hung, and an upper clamp mechanism and a lower clamp mechanism arranged vertically opposite to each other in the measuring zone, wherein the upper clamp mechanism includes a pair of upper clamp arms for interposedly holding an upper clamped portion of the test sample piece positioned inward of an upper end of the test sample piece therebetween and the lower clamp mechanism includes a pair of lower clamp arms for interposedly holding a lower clamped portion of the test sample piece positioned inward of a lower end of the test sample piece therebetween.

BRIEF DESCRIPTION OF THE PREFERRED EMBODIMENT

These and other objects and many of the attendant advantages of the present invention will be readily appreciated as the same becomes better understood by reference to the following detailed description when considered in connection with the accompanying drawings in which like reference numerals designate like or corresponding parts throughout; wherein.

DETAILED DESCRIPTION OF THE PREFERRED EMBODIMENT

Now, a physical property measuring device according to the present invention will be described hereinafter with reference to the accompanying drawings.

Figure 1:
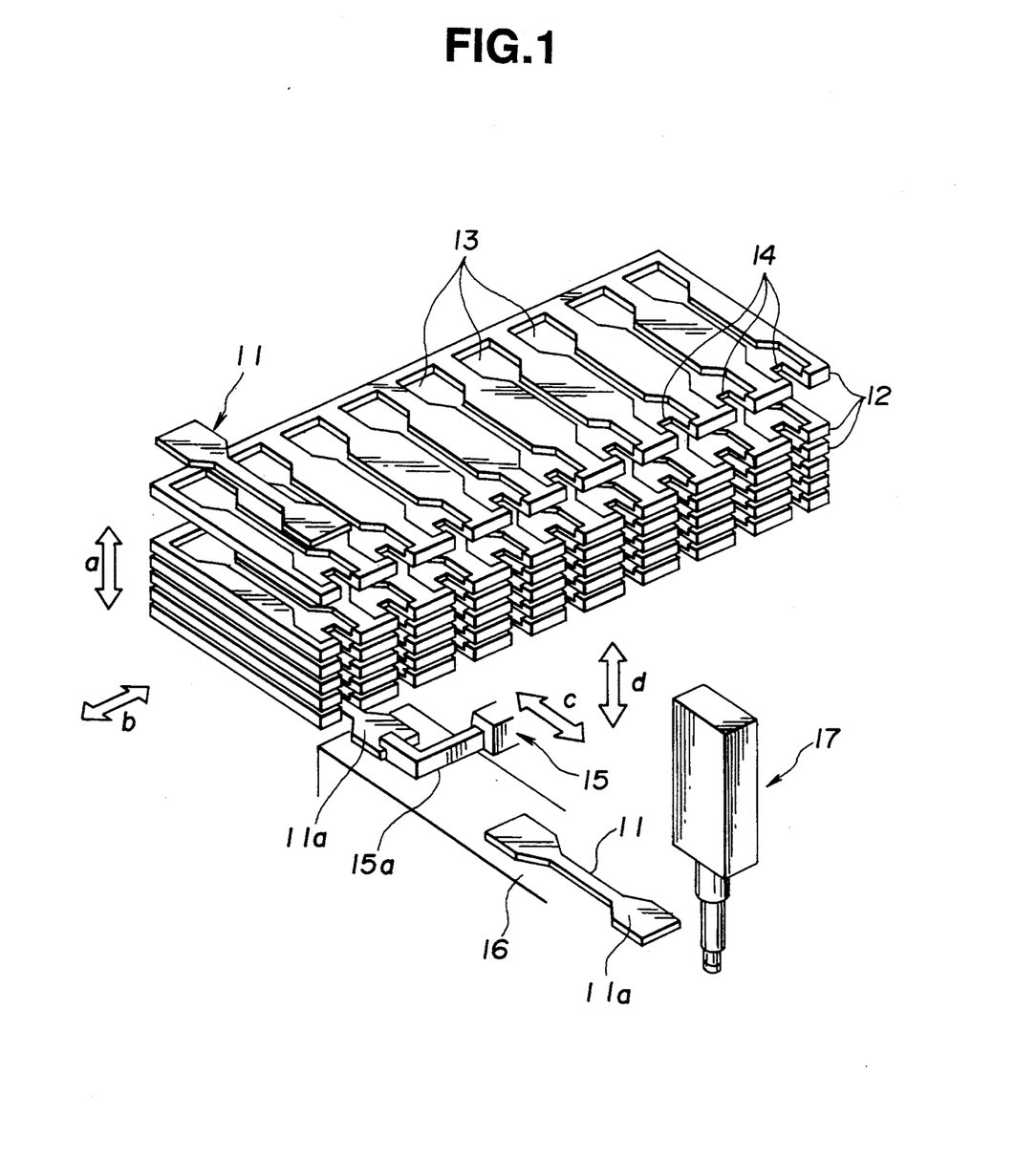
FIG. 1 is a schematic perspective view generally showing a mechanism for feeding a test sample piece in a physical property measuring device according to an embodiment of the present invention.

Referring first to FIG. 1, a test sample piece feed mechanism incorporated in a physical property measuring device according to an embodiment of the present invention is illustrated, wherein reference numeral 11 designates a test sample piece of which physical properties are to be measured. In the illustrated embodiment, the test sample piece may be in the form of, for example, a flexible sheet such as a flexible film.

The physical property measuring device of the illustrated embodiment includes at least one sample stocker 12 which is formed with a plurality of storage grooves 13 of a shape corresponding to the test sample piece 11 in a manner to be juxtaposed to each other. The storage grooves 13 each are open at one end or an extraction side end thereof through each of cutouts 14 formed at each of the sample stockers 12, so that the test sample piece may be extracted from each of the storage grooves 13. In the illustrated embodiment, a plurality of such sample stockers 12 are arranged in a so as to be vertically spaced from each other at predetermined intervals, to thereby form a sample stocker group. The sample stocker group thus formed is controllably movable in a vertical direction indicated by arrows a and a lateral direction indicated by arrows b. The vertical direction a corresponds to a direction of vertical arrangement of the sample stockers 12 and the lateral direction b corresponds to a direction of arrangement of the storage grooves 13 in juxtaposition to each other in each of the sample stockers 12.

The physical property measuring device of the illustrated embodiment also includes a holding mechanism 15 for interposingly holding the test sample piece 11. The holding mechanism 15 includes a pair of holding arms 15a for vertically interposingly holding the test sample piece 11 therebetween. The holding arms 15a are constructed in manner to be controllably openable with respect to each other so as to interposingly hold the test sample piece 11 therebetween and accessible to the test sample piece 11 through the cutout 14 in a longitudinal direction indicated at arrows c in FIG. 1, to thereby extract the test sample piece 11 from the storage groove 13 as shown in FIG. 1. The physical property measuring device further includes a transfer and support mechanism 16 for transferring, to a measuring zone provided at a device body 17 of the physical property measuring device, the test sample piece extracted from the storage groove 13 by the holding mechanism and supporting the test sample piece thereon. In the illustrated embodiment, the physical device measuring device may be in the form of a thickness measuring device and the support. The transfer and support mechanism 16 is arranged in close proximity to an extraction side of the sample stocker 12.

Now, the manner of operation of the physical property measuring device of the illustrated embodiment constructed as described above will be described hereinafter with reference to FIG. 1.

First, test sample pieces 11 of which physical properties are to be measured are stored in the storage recessions 13 of each of the sample stockers 12. The sample stockers 12 thus filled with the test sample pieces 11 are superposedly arranged so as to be vertically spaced from each other at predetermined intervals while being kept horizontal, resulting in the sample stocker group being formed. Then, the sample stocker group thus formed is controllably moved in the directions of the arrows a and b, so that the extraction side of the storage groove in which the test sample to be first tested is stored is positioned in proximity to the transfer and support mechanism 16. In FIG. 1, the sample stocker group is moved so that a lowermost storage groove 13 on a left-extremity side is positioned in proximitry to the transfer and support mechanism 16.

Then, the holding arms 15a of the holding mechanism 15 are inserted at a distal end thereof into the cutout 14 as indicated at the arrows c while keeping the holding arms 15a of the holding mechanism 15 separated from each other or open with respect to each other. Then, the holding arms 15a are closed with respect to each other to vertically firmly hold an extraction side end 11a of the test sample piece 11 therebetween in a manner to interpose it therebetween.

Subsequently, the holding mechanism 15 is moved in the longitudinal direction of the arrows c for the purpose of extracting the test sample piece 11 thus vertically interposedly held between the holding arms 15a of the holding mechanism 15 from the sample stocker group while the holding mechanism 15 is moved somewhat in the vertical direction of the arrows d or in a downward direction, so that the test sample piece 11 interposedly held between the holding arms 15a may be extracted from the storage groove 13 onto the transfer and support mechanism 16 while being kept raised from the storage groove 13. Finally, actuation of the transfer and support mechanism 16 permits the test sample piece 11 to be fed to the measuring zone of the body 17 of the thickness measuring device.

Thus, the physical property measuring device of the illustrated embodiment is so constructed that extraction of the test sample piece 11 from the sample stocker 12 is carried out by merely interposedly holding the extraction side end 11a of the test sample piece 11 between the holding arms 15a of the holding mechanism 15 and then putting it on the transfer and support mechanism 16. Such construction effectively eliminates an adverse effect of any unnecessary external force on the test sample piece which is encountered with use of the suction means in the prior art described above. This results in effectively preventing the test sample piece from being deformed or wrinkled, to thereby permit the test sample piece to be maintained in the form suitable for measurement of the thickness.

In addition, the physical property measuring device of the illustrated embodiment may be so operated that the sample stocker group is moved by a distance corresponding to an interval between the storage grooves 13 adjacent to each other in the lateral direction of the arrows b and then the abovedescribed operation is repeated. This permits the test sample piece 11 stored in the laterally adjacent storage groove 13 to be fed to the measuring zone of the device body 17 of the physical property measuring device. Further, controlled movement of the sample stocker group in the vertical direction indicated by the arrows and permits the vertically adjacent test sample piece 11 to be extracted for the measurement.

Figure 2:
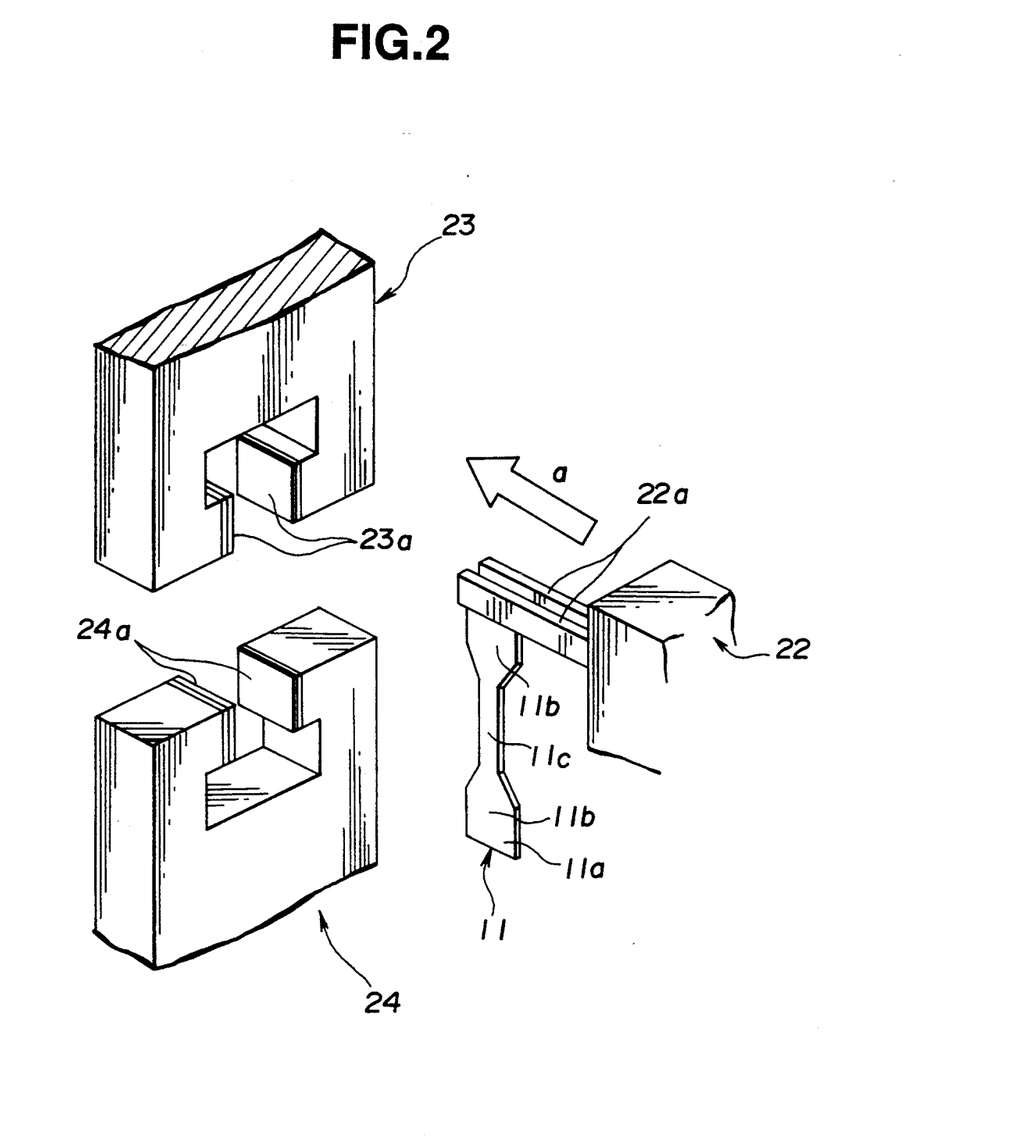
FIG. 2 is a fragmentary schematic perspective view showing transfer of a test sample piece to a measuring zone in a physical property measuring device according to an embodiment of the present invention.

Now, the measuring zone of the physical property measuring device of the illustrated embodiment will be described hereinafter with reference to FIGS. 2 and 3.

Reference numeral 22 designates a transfer mechanism for transferring the test sample piece 11, which mechanism includes a pair of feed or transfer arms 22a arranged so as to forwardly horizontally extend therefrom and be openable with respect to each other. The transfer arms 22a are adapted to interposedly hold therebetween an upper end 11a of the test sample piece fed through the transfer and support mechanism 17 to the transfer mechanism 22 and then transfer it to the measuring zone of the physical property measuring device while keeping it hanging.

Also, the physical property measuring device of the illustrated embodiment includes one set of upper and lower clamp mechanisms 23 and 24 which are arranged so as to be opposite to each other in the vertical direction. The upper clamp mechanism 23 includes a pair of upper clamp arms 23a arranged laterally opposite to each other and constructed so as to be controllably open with respect to each other and likewise the lower clamp mechanism 24 includes a pair of lower clamp arms 24a arranged laterally opposite to each other and constructed so as to be controllably open with respect to each other. The upper clamp arms 23a are adapted to firmly interposedly hold therebetween an upper clamped portion 11b of the test sample piece 11 defined inward of the upper end 11a of the test sample piece 11 and the lower clamp arms 24a are adapted to firmly interposedly hold therebetween a lower clamped portion 11b of the piece 11 defined inward of the lower end 11a of the test sample piece 11, so that the test sample piece 11 may be subject to a desired tensile test.

Controllable opening of the transfer arms, upper clamp arms 23a and lower clamp arms 24a may be carried out by means of any suitable mechanism such as, for example, an air jaw mechanism which uses compressed air as a drive source or the like.

Such support of the test sample piece 11 while hanging positively eliminates an adverse effect of any unnecessary external force on the test sample piece which is encountered with use of the suction means in the prior art described above. This results in effectively preventing the test sample piece 11 from being deformed or wrinkled, to thereby permit the test sample piece to be maintained in the form suitable for measurement of the thickness. Then, the transfer mechanism 22 is advanced in a direction indicated by an arrow a in FIG. 2 while keeping the test sample hanging, resulting in the test sample piece 11 being transferred to the measuring zone of the physical property measuring device.

Figure 3:
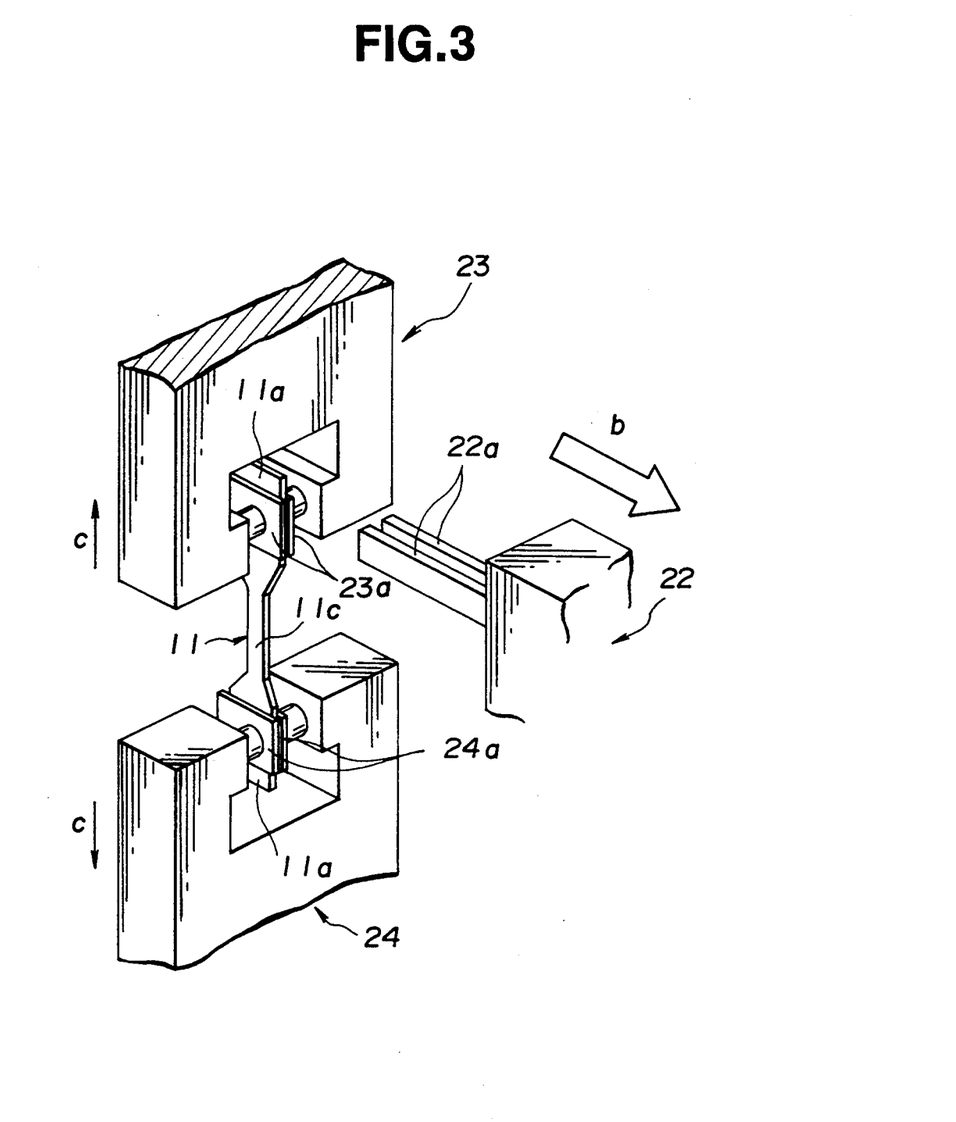
FIG. 3 is a fragmentary schematic perspective view showing clamping of a test sample piece in a physical property measuring device according to an embodiment of the present invention, wherein upper and lower ends of the test sample piece are clamped by one set of a pair of upper holding arms and a pair of lower holding arms, respectively.

Then, in the upper and lower clamp mechanisms 23 and 24 arranged in the measuring zone, the upper clamp arms 23a and lower clamp arms 24a in each pair kept open with respect to each other are actuated so as to firmly interposedly hold therebetween the upper and lower clamped portions 11b of the test sample piece 11 defined inward of the upper and lower ends 11a thereof, respectively, as shown in FIG. 3. Then, the transfer mechanism 22 is rearwardly moved or retracted in a direction indicated by an arrow b in FIG. 3 and the upper and lower clamp mechanisms 23 and 24 are moved in directions opposite to each other as indicated by arrows c in FIG. 3 to apply tensile force to the clamped test sample piece 11, resulting in a desired tensile test being carried out with respect to the test sample piece.

The test sample piece includes an intermediate measured section 11c, at which rupture of the test sample piece in the test for measuring the physical properties is carried out. After completion of the test, one of fragments of the ruptured test sample piece or the upper clamped portion 11b of the ruptured test sample piece 11 is kept held between the upper clamp arms 23a and the other fragment or the lower clamped portion 11b is kept held between the lower clamp arms 24a while the upper and lower ends 11a of the ruptured test sample pieces 11 kept from application of tensile force thereto are kept outwardly projected from the upper and lower clamp arms 23a and 24a. Therefore, the upper and lower clamped portions 11b or fragments of the ruptured test sample piece kept adhered to clamping surfaces of the clamp arms even after the clamp arms are actuated so as to be open with respect to each other can be highly easily and automatically removed from the clamping surfaces as desired utilizing the projected upper and lower ends 11a.

Also, additional use of an auxiliary guide mechanism which will be described hereinafter permits the test sample piece 11 to be more conveniently guided from the upper clamp mechanism 23 to the lower clamp mechanism 24.

Such an auxiliary guide mechanism may be constructed of two or more arms arranged opposite to each other so as to interpose the test sample piece 11 therebetween. More particularly, it may be constructed of two or more arm members arranged so as to be movable in parallel with each other from between the upper clamp arms and the lower clamp arms to below the lower clamp arms. Alternatively, it may be constructed of a suction nozzle arranged on a line extending between the upper clamp arms and the lower clamp arms and outside the lower clamp arms. The auxiliary guide mechanism of the former construction is particularly preferably applied.

Now, the auxiliary guide mechanism of the former construction will be described hereinafter.

Figure 4:
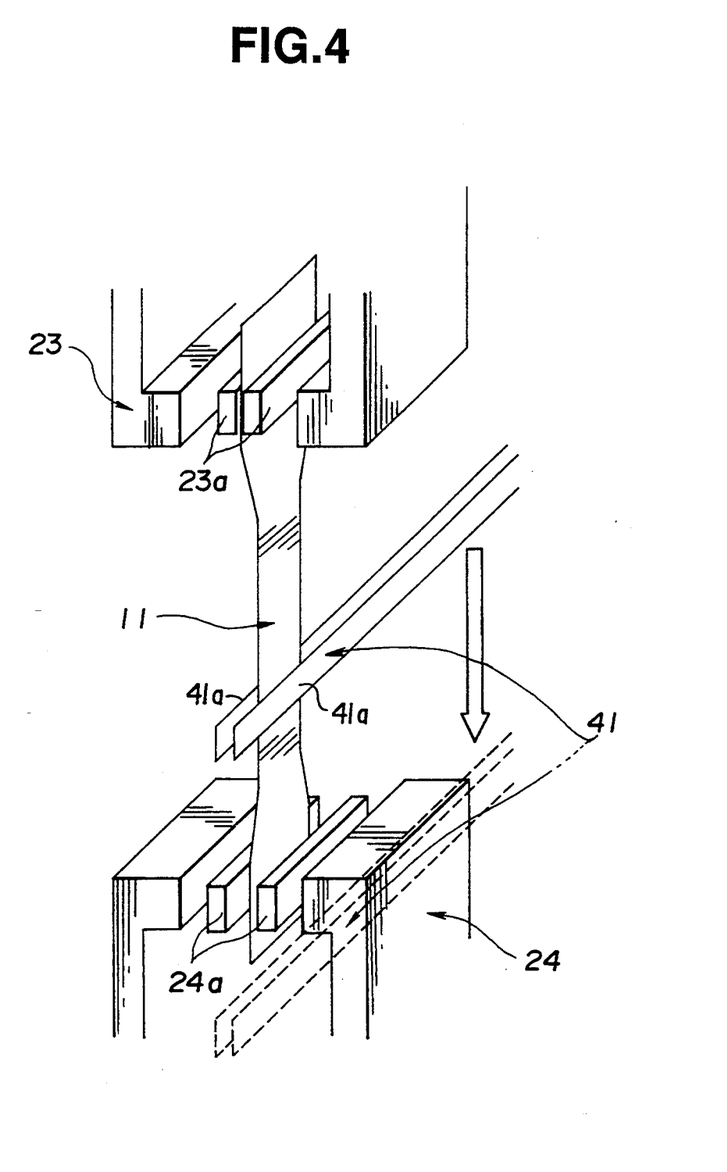
FIG. 4 is a fragmentary schematic perspective view showing an auxiliary guide mechanism.

The auxiliary guide mechanism, as shown in FIG. 4, includes an auxiliary guide arm 41 comprising two arm members 41a arranged opposite to each other so as to interposedly hold the test sample piece 11 therebetween and between the upper clamp mechanism 23 and the lower clamp mechanism 24. The two arm members 41a constituting the auxiliary guide arm 41 are arranged so as to be spaced from each other at an interval of about 1 to 10 mm, to thereby be substantially prevented from being contacted with the test sample piece 11. This effectively prevents the auxiliary guide arm 41 from damaging the test sample piece 11.

In the auxiliary guide arm 41 constructed as described above, the test sample piece 11 is transferred to the upper clamp mechanism 23 arranged above the measuring zone by means of the transfer mechanism 22, resulting in being interposedly held between the upper clamp arms 23a. At this time, the lower clamp arms are kept open with respect to each other. The auxiliary guide arm 31 is initially located at a position at solid lines in FIG. 4 or at an intermediate position between the upper clamp mechanism 23 and the lower clamp mechanism 24.

Then, the auxiliary guide arm 41 is downwardly moved to a position below the lower clamp mechanism 24 or a position indicated at broken lines in FIG. 4. At this time, when the test sample piece 11 is curved or deformed to the degree of failing to permit the lower clamped portion of the test sample piece 11 from being positioned between the lower clamp arms 24a of the lower clamp mechanism 24, downward movement of the auxiliary guide arm 41 results in the test sample piece 11 being guided to a proper position between the lower clamp arms 24a. After the auxiliary guide arm 41 guides the test sample piece 11 to the proper position between the lower clamp arms 24a, the lower clamp arms 24a firmly hold the test sample piece 11 in a manner to interpose it therebetween.

Figure 5:
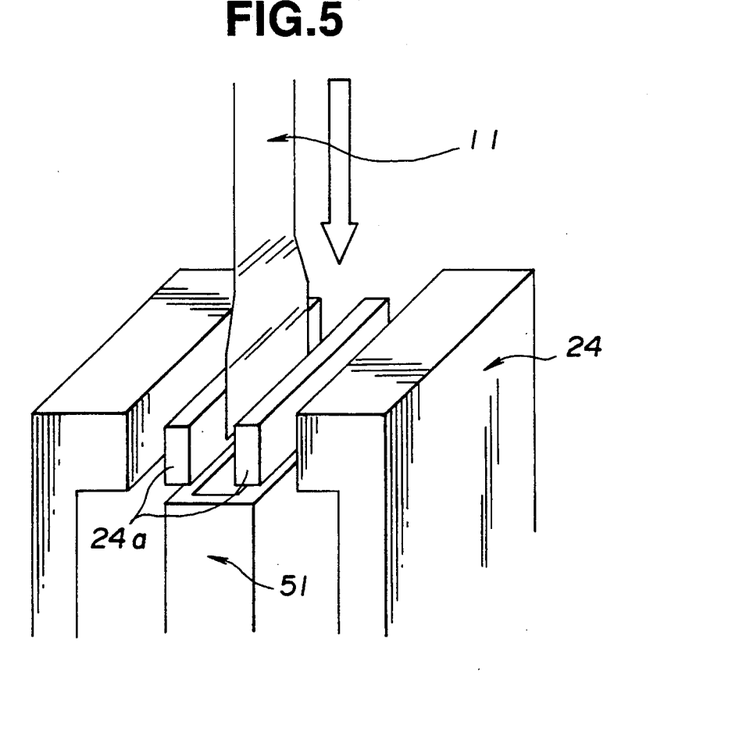
FIG. 5 is a fragmentary enlarged schematic perspective view of the auxiliary guide mechanism shown in FIG. 4.

Referring now to FIG. 5, an extension indicator in which a suction nozzle is used as the auxiliary guide mechanism is schematically illustrated. In the extension indicator of FIG. 5, a suction nozzle 51 is used as the auxiliary guide mechanism in place of the auxiliary guide arm 41 shown in FIG. 4. The suction nozzle 51 is arranged below the lower clamp mechanism 24. The test sample piece 11 is held between the upper clamp arms 23a of the upper clamp mechanism and then guided at the lower clamped portion thereof to the lower clamp mechanism 24 due to actuation of the suction nozzle 51, resulting in being held between the lower clamp arms 24a of the lower clamp mechanism 24.

In addition, as described above, even when each pair of clamp arms are rendered open with respect to each other, it is often seen that one end of each of the fragments of the ruptured test sample piece is kept adhered to a clamp surface of one of the clamp arms. Thus, it is preferable to provide the clamp arm with a mechanism for removing the fragment therefrom. Such a removal mechanism may be constructed an upper removal arm for clamping an upper end of the test sample piece to remove the fragment held by said upper clamp arms therefrom and a lower removal arm for clamping a lower end of the test sample piece to remove the fragment held by said lower clamp arms therefrom.

Figure 6:
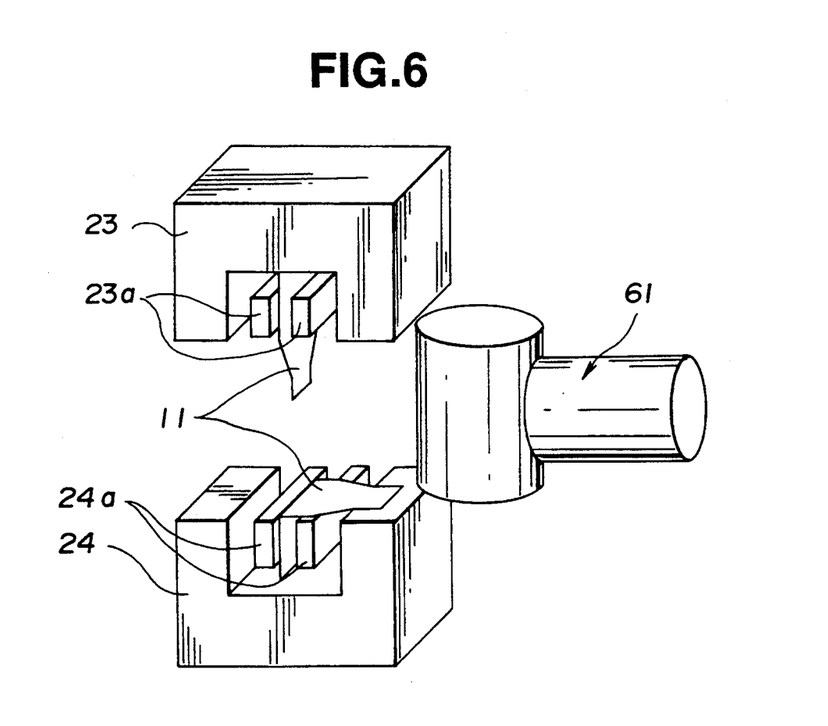
FIG. 6 is a schematic perspective view showing a mechanism for removing fragments of a test sample ruptured in a test for measuring physical properties of a test sample piece.

Alternatively, as shown in FIG. 6, the test sample piece 11 is ruptured in a test of measuring the physical properties such as breaking extension or the like, so that the test sample piece is divided into two fragments comprising an upper fragment held between the upper clamp arms 23a and a lower fragment held between the lower clamp arms 24a. Reference numeral 61 designates a suction arm which acts as a fragment removal mechanism. The suction arm 61, as shown in FIG. 6, is generally formed into a substantially T-shape. More particularly, the suction arm 61 includes a distal end section formed into a pipe-like shape having a vertically extending axis and a connection pipe section for connecting the distal end section to a suction blower (not shown) therethrough. The connection pipe section is made of a flexible pipe and arranged so that a central axis thereof extends in a horizontal direction. The suction arm 61 is provided with a transfer mechanism (not shown) which acts to move the suction arm 61 between the measuring zone and a position between the upper clamp mechanism 23 and the lower clamp mechanism 24. The distal end section of the suction arm 61 is formed into an inner diameter larger than a width of the test sample piece 11. The connection pipe section of the suction arm 61 for connecting the distal end section to the suction blower (not shown) is made of a flexible material such as a flexible tube or the like and formed into an inner diameter larger than a width of the test sample piece. The suction blower may be constructed in any suitable manner so long as it can remove the test sample piece by suction. For example, a motorized suction blower may be used as the suction blower.

Now, removal of the fragments of the ruptured test sample piece carried out by the suction arm 61 after measurement of physical properties of the test sample piece will be described hereinafter.

After the measurement, a cross head (not shown) is moved to cause a distance between the upper clamp mechanism 23 and the lower clamp mechanism 24 to be slightly increased as compared with a length of the distal end section of the suction arm 61. Then, the suction arm 61 is moved to a position between the upper clamp mechanism 23 and the lower clamp mechanism 24 and then the upper clamp arms 23a and lower clamp arms 24a are actuated so as to be open with respect to each other, respectively, while actuating the suction blower (not shown), resulting in the fragments of the ruptured test sample piece being removed by suction. Thereafter, the actuation of the suction blower is stopped and then the suction arm 61 is outwardly moved from the measuring zone. Finally, the upper and lower clamp mechanisms 23 and 24 are returned to the original position for preparation for feeding of the next test sample piece to the measuring zone.

As can be seen from the foregoing, the physical property measuring device of the present invention which is directed to measurement of physical properties of a test sample piece in the form of a flexible sheet-like material such as a flexible film is so constructed that the test sample piece is fed to the measuring zone of the physical property measuring device while being interposedly held at the whole upper end thereof between the transfer arms so as to be kept hanging, to thereby minimize or substantially prevent application of any unnecessary external force thereto. Also, in the measuring zone, the test sample piece is kept interposedly held at the upper and lower clamped portions thereof inward of the upper and lower ends thereof between the upper clamp arms of the upper clamp mechanism and then the upper and lower clamp mechanisms are actuated relative to each other to carry out measurement of desired physical properties. Such construction effectively prevents any unnecessary external force from being applied to the test sample piece during feeding of the test sample piece to the measuring zone, resulting in the test sample piece being satisfactorily fed to the measuring zone while being kept in the form suitable for a test of the physical properties. Also, the above-described construction of the present invention, after completion of the test, permits the fragments of the ruptured test sample piece adhered to the clamp arms to be readily removed therefrom through the upper and lower ends of the fragments of the ruptured test sample piece which are vertically outwardly projected from the clamp arms.

Further, the physical property measuring device of the present invention includes the sample stocker group including a plurality of the sample stockers each formed with the storage grooves which are arranged in juxtaposition to each other and of which the extraction side is open through the cutout and arranged so as to be controllably moved, the holding mechanism for extracting the test sample piece from the storage groove through the cutout while interposedly holding it thereon, the transfer and support mechanism arranged in proximity to the extraction side of the sample stocker group for supporting the test sample piece extracted by the holding mechanism while transferring it. Thus, the physical property measuring device of the present invention permits the test sample piece to be fed from the sample stocker to the measuring zone while preventing any unnecessary external force from being applied to the test sample piece during extraction of the test sample piece from the sample stocker, so that feeding of the test sample piece to the measuring zone may be readily and stably accomplished to ensure measurement of the physical properties with high reliability.

Moreover, employment of the auxiliary guide means for guiding the test sample piece from the upper clamp mechanism to the lower clamp mechanism further promotes stable measurement of the physical properties.

Furthermore, the present invention is so constructed that the mechanism for removing the fragments of the test sample piece ruptured in the test may be moved between the upper clamp mechanism and the lower clamp mechanism to remove the fragments held on the upper and lower clamp mechanism therefrom by suction. Such construction permits the removal to be readily accomplished, resulting in automatic measurement of breaking extension of a flexible film and the like which is difficult or troublesome in the prior art being continuously and stably carried out.

While a preferred embodiment of the invention has been described with a certain degree of particularity with reference to the drawings, obvious modifications and variations are possible in light of the above teachings. It is therefore to be understood that within the scope of the appended claims, the invention may be practiced otherwise than as specifically described.

What is claimed as new and desired to be secured by letters patent of the United States is:

1. A physical property measuring device for measuring physical properties of a test sample piece of a flexible sheet material, comprising:
    a measuring zone in which measurement of physical properties of the test sample piece is carried out;
    a transfer mechanism including a pair of transfer arms which transfer the test sample piece of said measuring zone while interposedly hanging and holding the test sample piece from one end thereof between said transfer arms;
    an upper clamp mechanism and a lower clamp mechanism arranged vertically opposite each other in said measuring zone;
    said upper clamp mechanism including a pair of upper clamp arms interposedly holding an upper clamped portion of the test sample piece positioned inward of an upper end of the test sample therebetween; and
    said lower clamp mechanism including a pair of lower clamp arms interposedly holding a lower clamped portion of the test sample piece positioned inward of a lower end of the test sample piece therebetween.

2. A physical property measuring device as defined in claim 1, wherein said upper and lower clamp arms each comprise an air jaw type arm using compressed air as a drive source.

3. A physical property measuring device for measuring physical properties of a test sample piece of a flexible sheet material, comprising:
    a measuring zone in which measurement of physical properties of the test sample piece is carried out;
    a transfer mechanism including a pair of transfer arms which transfer the test sample piece to said measuring zone while interposedly hanging and holding the test sample piece from one end thereof between said transfer arms;
    an upper clamp mechanism and a lower clamp mechanism arranged vertically opposite each other in said measuring zone;
    said upper clamp mechanism including a pair of upper clamp arms which interposedly hold therebetween an upper clamped portion of the test sample piece positioned inward of an upper end of the test sample piece;
    said lower clamp mechanism including a pair of lower clamp arms interposedly holding therebetween a lower clamped portion of the test sample piece positioned inward of a lower end of the test sample piece subsequent to said holding of the upper clamped portion of the test sample piece by said upper clamp arms; and
    a guide mechanism which guides said lower clamped portion of the test sample piece to said lower clamp arms subsequent to said holding of the upper clamped portion of the test sample piece by said upper clamp arms and prior to said holding of the lower clamped portion of the test sample piece by said lower clamp arms wherein said guide mechanism includes a pair of parallelly oriented arms movable along a length direction of said test sample piece.

4. A physical property measuring device for measuring physical properties of a test sample piece of a flexible sheet material, comprising:
    a measuring zone in which measurement of physical properties of the test sample piece is carried out;
    a transfer mechanism including a pair of transfer arms which transfer the test sample piece to said measuring zone while interposedly hanging and holding the test sample piece between said transfer arms;
    an upper clamp mechanism and a lower clamp mechanism arranged vertically opposite each other in said measuring zone;
    said upper clamp mechanism including a pair of upper clamp arms which interposedly hold therebetween an upper clamped portion of the test sample piece positioned inward of an upper end of the test sample piece;
    said lower clamp mechanism including a pair of lower clamp arms interposedly holding therebetween a lower clamped portion of the test sample piece positioned inward of a lower end of the test sample piece subsequent to said holding of the upper clamped portion of the test sample piece by said upper clamp arms; and
    a guide mechanism which guides said lower clamped portion of the test sample piece to said lower clamp arms subsequent to said holding of the upper clamped portion of the test sample piece by said upper clamp arms and prior to said holding of the lower clamped portion of the test sample piece by said lower clamp arms, wherein said guide mechanism comprises an auxiliary guide arm which includes at least two arm members arranged opposite each other with the test sample piece being interposed therebetween and so as to be movable parallel with each other from a position between said upper clamp arms and said lower clamp arms to a position below said lower clamp arms.

5. A physical property measuring device as defined in claim 3, wherein said guide mechanism comprises a suction nozzle arranged on an extension of a line defined by connecting said upper clamp arms and lower clamp arms to each other and below said lower clamp arms.

6. A physical property measuring device for measuring physical properties of a flexible sheet-like test sample piece of a flexible sheet material, comprising:
- a measuring zone in which measurement of physical properties of the test sample piece is carried out;
- a transfer mechanism including a pair of transfer arms which transfer the test sample piece to said measuring zone to feed said measuring zone with the test sample piece while interposedly hanging and holding the test sample piece from one end thereof between said transfer arms;
- an upper clamp mechanism and a lower clamp mechanism arranged vertically opposite each other in said measuring zone;
- said upper clamp mechanism including a pair of upper clamp arms interposedly holding an upper clamped portion of the test sample piece positioned inward of an upper end of the test sample piece therebetween;
- said lower clamp mechanism including a pair of lower clamp arms interposedly holding a lower clamped portion of the test sample piece positioned inward of a lower end of the test sample piece therebetween; and
- a guide mechanism which removes fragments of the test sample piece ruptured due to measurement of the physical properties and which is held on said clamp arms.

7. A physical property measuring device for measuring physical properties of a flexible sheet-like test sample piece of a flexible sheet material, comprising:
- a measuring zone in which measurement of physical properties of the test sample piece is carried out;
- a transfer mechanism including a pair of transfer arms which transfer the test sample piece to said measuring zone to feed said measuring zone with the test sample piece while interposedly hanging and holding the test sample piece between said transfer arms;
- an upper clamp mechanism and a lower clamp mechanism arranged vertically opposite each other in said measuring zone;
- said upper clamp mechanism including a pair of upper clamp arms interposedly holding an upper clamped portion of the test sample piece positioned inward of an upper end of the test sample piece therebetween;
- said lower clamp mechanism including a pair of lower clamp arms interposedly holding a lower clamped portion of the test sample piece positioned inward of a lower end of the test sample piece therebetween; and
- a removal mechanism which removes fragments of the test sample piece ruptured due to measurement of the physical properties and which is kept held on said clamp arms, wherein said removal mechanism comprises a suction arm arranged so as to be movable to a position between said upper clamp arms and said lower clamp arms to remove said fragments by suction.

8. A physical property measuring device for measuring physical properties of a flexible sheet test sample piece of a flexible sheet-like material, comprising:
- a measuring zone in which measurement of physical properties of the test sample piece is carried out;
- a transfer mechanism including a pair of transfer arms which transfer the test sample piece to said measuring zone to feed said measuring zone with the test sample piece while interposedly handing and holding the test sample piece between said transfer arms;
- an upper clamp mechanism and a lower clamp mechanism arranged vertically opposite each other in said measuring zone;
- said upper clamp mechanism including a pair of upper clamp arms interposedly holding an upper clamped portion of the test sample piece positioned inward of an upper end of the test sample piece therebetween;
- said lower clamp mechanism including a pair of lower clamp arms interposedly holding a lower clamped portion of the test sample piece positioned inward of a lower end of the test sample piece therebetween; and
- a removal mechanism which removes fragments of the test sample piece ruptured due to measurement of the physical properties and which is held on said clamp arms, wherein said removal mechanism comprises an upper removal arm clamping an upper end of the test sample piece to remove the fragment held by said upper clamp arms therefrom and a lower removal arm clamping a lower end of the test sample piece to remove the fragment held by said lower clamp arms therefrom.

9. A physical property measuring device for measuring physical properties such as tensile strength or the like of a test sample piece of a flexible sheet material, comprising:
- a measuring zone in which measurement of physical properties of the test sample piece is carried out;
- a plurality of parallel sample stockers each of which is formed with a plurality of storage grooves storing the test sample pieces therein and a plurality of cutouts;
- said storage grooves being arranged in spaced juxtaposition with each other;
- said cutouts being arranged so as to permit an extraction side of each of said storage grooves on which the test sample piece is extracted from said storage groove to be open through each of said storage grooves;
- a sample extraction mechanism including holding arms and arranged so as to be accessible to each of said cutouts of said storage grooves, said holding arms interposedly holding the test sample piece therebetween to outwardly extract it from said storage groove through said cutout;
- a transfer and support mechanism arranged in proximity to said extraction side of said sample stocker which transfers the test sample piece extracted from said sample stocker while hanging from one end thereof on said transfer and support mechanism;

a transfer mechanism transferring the test sample piece to said measuring zone while keeping the test sample piece hanging from said one end; and an upper clamp mechanism and a lower clamp mechanism arranged vertically opposite to each other in said measuring zone;

said upper clamp mechanism including a pair of upper clamp arms interposedly holding an upper clamped portion of the test sample piece positioned inward of an upper end of the test sample piece therebetween;

said lower clamp mechanism including a pair of lower clamp arms interposedly holding a lower clamped portion of the test sample piece positioned inward of a lower end of the test sample piece therebetween.

* * * * *

UNITED STATES PATENT AND TRADEMARK OFFICE
CERTIFICATE OF CORRECTION

PATENT NO. : 5,437,192
DATED : August 1, 1995
INVENTOR(S) : Takeshi KAWAMOTO, et al.

It is certified that error appears in the above-indentified patent and that said Letters Patent is hereby corrected as shown below:

On the title page, Item [75], the second inventor's name should read:

--Toshio Hirowatari--

Signed and Sealed this

Fourteenth Day of November, 1995

Attest:

BRUCE LEHMAN

*Attesting Officer*        *Commissioner of Patents and Trademarks*